United States Patent [19]

Goodman

[11] Patent Number: 5,053,391

[45] Date of Patent: Oct. 1, 1991

[54] COMPOSITION CONTAINING POLYPEPTIDE HORMONE FOR STIMULATING SKLETAL GROWTH IN POULTRY

[75] Inventor: Geoffrey Goodman, Kibbutz Amiad, Israel

[73] Assignee: Migal Galilee Technological Center Ltd., Israel

[21] Appl. No.: 204,571

[22] Filed: Jun. 9, 1988

[30] Foreign Application Priority Data

Jun. 15, 1987 [IL] Israel ......................................... 82885

[51] Int. Cl.$^5$ ...................... A61K 37/02; A61K 37/36
[52] U.S. Cl. .......................................... 514/12; 514/2; 514/21; 530/854; 530/399
[58] Field of Search ................ 514/12, 2, 21; 530/854, 530/399

[56] References Cited

U.S. PATENT DOCUMENTS 3,265,580  8/1966  Nelson .................................. 530/854
3,317,392  5/1967  Eppstein .................................. 514/2

OTHER PUBLICATIONS

Lewis et al., Biochem. Biophys. Res. Comm., 44, No. 5, 1169–1176 (1971).
The Pharmaceutical Basis of Therapeutics, 3rd ed., Goodman & Gilman, The MacMillan Company, N.Y., 1965, p. 1567.
American College Dictionary (1964 Ed), definition of "Anabolism".
A. L. Lehninger, Biochemistry, 2 ed (Worth Pub. 1975), pp. 369–374.
S. M. Russell et al., Life Sciences, 23: 2373–2382 (1978), Summary only.
Textbook of Endocrinology, 6th Ed. R. H. Williams Ed; (Saunders Co., Philadelphia, 1981), Chapter 3, "The Adenohypophysis", p. 85.
Ibid, Chapter 28, "Hormones in Normal and Aberrant Growth", p. 1149.
L. G. Raisz et al., Ann. Rev. Physiol., 43, 225–238 (1981) Abstract only.
C. G. Scanes et al., (Scanes I), Gen. Comp. Endocrinol., 27:371–379 (1975), Abstract and page 378.
C. G. Scanes et al., (Scanes II), Life Sciences 28:2895–2902 (1981), Abstract and papers therefrom.
C. G. Scanes et al., (Scanes III), Poultry Science, 63: 2062–2074 (1984) Abstract.
D. B. King et al., Proc., Soc. Exp. Biol. Med., 182:201–207 (1986) Abstract.
W. H. Burke et al., Endocrinology, 120:651–658 (1987), Abstract.
A. L. Lehninger, Principals of Biochemistry (Worth Pub. 1982), pp. 337–338.
Textbook of Endocrinology, 6th Ed., R. H. Williams Ed; (Saunders Co., Philadelphia, 1981) pp. 401 and 1153.
Duke's Physcology of Domestic Animals, 10th EP, M. J. Stwensen, Ed. (Cornell Univ. Pres. 1984); Chapter 48, "Endocrine Gland", pp. 770–771.
C. G. Jones et al. Gen. and Comparative Endocrinology; 27:371–379 (1975). Only pp. 371 and 378 available now.
D. B. King et al., Proc. Soc. Exper. Biol. and Med., 182:201–207 (1986) Abstract only available.
S. C. Scones et al., "Growth Hormone in Poultry", Poultry Science, 63:2062–2074 (1984) Abstract only.
C. G. Scones et al., Life Sciences 28:2898–2902 (1981) Summary and experts.

Primary Examiner—F. T. Moezie
Attorney, Agent, or Firm—Silverman, Cass & Singer

[57] ABSTRACT

The invention provides a method for stimulating skeletal growth in normal poultry as evidenced by increased metatarsal length of treated poultry comprising administering a growth stimulating amount of prolactin to said poultry.

7 Claims, No Drawings

COMPOSITION CONTAINING POLYPEPTIDE HORMONE FOR STIMULATING SKLETAL GROWTH IN POULTRY

BACKGROUND OF THE INVENTION

1. Field of the Invention

The present invention relates to a method and composition for stimulating skeletal growth in normal poultry.

More particularly the present invention relates to a method and composition for stimulating growth in normal poultry involving the administration of a pituitary peptide hormone.

2. Description of Related Art

Physiological action on tissues by one of the pituitary peptide hormones is usually essential for growth in vertebrates. One such peptide, Growth Hormone (GH, also known as somatotrophin), has attracted most attention, partly because of its proved importance in human growth. It also stimulated growth in studies on other (mainly mammalian) species. Prolactin (PRL) is a similar pituitary peptide. Due to its stimulus to the development of mammary tissue, PRL has usually been regarded as a lactogenic hormone. In birds, it has been studied particularly for its part in reproductive and maternal behavioural processes. Thus it is involved in fattening of migratory species, influences brooding and stimulates production of pigeon 'milk'(sloughed gastric mucosa). Indeed, this forms the basis of a classical test for lactogenicity, used to this day. Both GH and PRL have functions additional to those mentioned above. These vary from class to class and species to species and may be contradictory when comparing species with species. The relative roles of the two may also be exchanged between them. It is not surprising then, that there is a considerable degree of homology of aminoacid sequence between GH PRL. This is only 50% in humans, but higher in some other species. Nevertheless, with respect to the possible effects of each of the two hormones, interest in and positive evidence about the role of GH in growth is paramount, particularly in mammals. However, PRL stimulates tissue preservation and renewal, and growth and development in amphibians and reptiles, the latter class being phylogenetically close to birds. It also stimulates growth in juveniles of some rodent species.

Increase of weight alone (perhaps due to fat) without change in size, is inadequate evidence for growth stimulation by hormones. This is an important consideration when studying juvenile growth. The latter has been studied particularly in humans, GH having a positive growth effect and PRL, none. Hormonal influence on bird growth had been studied relatively little, until interest increased in recent years, because of the commercial potential of improved poultry growth. Work has been concentrated on GH. Initially, because of the difficulty in obtaining native hormone, studies were performed with bovine or ovine GH. Stimulation of growth was either absent or uncertain, although body fat seemed to be clearly reduced. Chicken GH is now more available. Produced in bacteria by several groups, using recombinant genetic technology, chicken GH has been administered with disappointing results. The effect on the growth of whole poultry birds by PRL administered alone, has not been known.

In an article published by D.B. King and C.G. Scaner in June 1986 (Proc. Soc. Expt. Biol. Med. 182:201-207) entitled Effect of Mammalian Growth Hormone and Prolactin on the Growth of Hypophysectomized Chickens, it is stated at the end of the abstract that "These results provide evidence that mammalian GH enhances body weight gain, bone growth and the growth of several organs in the hypophysectomized chicken. Mammalian PRL increased body weight gain, liver weight and adipose tissue weight in corticosterone-treated hypophysectomized chickens, but did not influence bone growth or the weights of the heart, pectoralis, thymi or bursa".

It is first to be noted that while said article teaches that administration of growth hormone can partially restore growth in an animal with restricted growth, there is no certainty that the same treatment will improve on normal growth in a normal animal. Nevertheless, one might, based on these results, try to stimulate poultry growth of normal poultry using growth hormone.

On the other hand, in light of the clear statement in said article that "mammalian PRL ... did not influence bone growth", one would naturally assume that PRL also would not influence bone growth in normal poultry.

It was, thus, extremely surprising to discover that contrary to the negative teaching of said article, prolactin in fact was effective for stimulating skeletal growth in normal poultry, as evidenced by increased metatarsal length as described hereinafter.

SUMMARY OF THE INVENTION

The present invention there is now provided a method for stimulating skeletal growth in normal poultry as evidenced by increased metatarsal length of treated poultry comprising administering a growth stimulating amount of prolactin to said poultry.

The prolactin can be ovine prolactin, chicken prolactin or prolactin obtained by cloning and bacterial expression of the chicken gene for prolactin by methods known per se. These materials are commercially available from Sigma Chemical (USA).

The term poultry used herein is intended to include all edible birds including water fowl, pigeons and ostriches.

The invention also provides a composition for stimulating skeletal growth in normal poultry as evidenced by increased metatarsal length of treated poultry comprising prolactin as active ingredient therein in combination with a veterinarally and toxicologically acceptable carrier.

The carrier used in formulating compositions of the present invention, can be any suitable carrier known per se and can preferably be simple sterile saline solution.

DETAILED DESCRIPTION OF THE INVENTION

In accordance with the present invention it is now also possible to administer both prolactin and growth hormone to said poultry either by, e.g., first administering prolactin to young poultry for several days and then subsequently administering growth hormone or by jointly administering prolactin and growth hormone to said poultry. Similarly prolactin and growth hormone could be administered to fertile eggs.

The administration of PRL and GH in combination can thus be used to cause a preferred ratio between leg length and the size of other parts of the skeleton. Formulations or methods in accordance with the invention are believed to offer potential in:

(a) accelerating the attainment of full growth of poultry thereby increasing feed conversion efficiency and reducing investment and labour costs by advancement of marketing;

(b) increasing the growth of such animals beyond the normal maximum;

(c) providing animals with physical conformation(s) designed to meet market and consumer preferences, changing from time to time.

In all cases, it is believed that the use of formulations and/or methods in accordance with the invention may offer significant cost saving advantages. Furthermore, administration of a PRL identical to the endogenous hormone, with or without chicken GH, could obtain advantageous growth without the possibly harmful residues from some other growth stimulants.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention. It is being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Preparative Example 1

Purified, lyophilized ovine PRL was obtained from Sigma Chemical Co. (U.S.A.) and dissolved in alkaline physiological saline (0.9%). This was later adjusted to physiological pH. Fresh material was prepared every two days and kept at +4° C. Concentration was adjusted to provide the daily dose of hormone in a volume of 0.5 ml of medium.

Biological Example 2

Cross-bred, male, day-old chickens of the heavy (Anak broiler) breed were obtained from a commercial source and housed in standard cages (five birds/cage), in an environment controlled at levels of temperature (32 reducing to 26 +/−1 degrees C.) and moisture (65% RH) conventional for age. The chicks were kept under continuous white fluorescent lighting, which varied from 80–120 lux between cages. Food and water were provided ad libitum. Nutrients in the diet were commercially conventional for age. Birds in experimental and control groups were paired for weight. Group means of metatarsal length were also similar at start of treatment. Injection of Prolactin i.m. in the leg was started at 15 days of age and continued for 21 days, the treated birds receiving 2.5 i.u./100 gm of body weight at 8:30 a.m. Control birds were injected with saline solution. Birds were weighed individually, daily during treatment and at 44 days when the experiment was terminated. The length of the metatarsus was measured weekly. from the start of treatment. Feed consumption was recorded, per cage.

Treated birds gained 6.5% more weight than the controls. More significantly, however, the legs of the Prolactin-treated birds were much longer on termination of the experiment, as judged by metatarsal length. This difference was highly significant ($p < 0.005$). Skin breaking strength was 17% greater in treated birds, so that dry matter other than fat was also 6.7% greater in these birds. This is presumably due to higher nitrogen levels which are expressed in greater collagen content. PRL is also known to increase collagen content in the integument of some reptiles and amphibians. There was also evidence of a difference in feed conversion efficiency.

The birds were killed by cervical dislocation. Abdominal fat and other internal tissues were removed and weighed.

Statistical Evaluation

Arithmetic means and standard errors were calculated using conventional methods. Statistically significant difference between groups were identified by Student's t-test.

TABLE 1

The Effect of Prolactin on Growth and Other Parameters in Male Broilers.

| | Prolactin | | Control |
|---|---|---|---|
| Body Weight[1] | | | |
| 15 days | 550 ± 18 | | 550 ± 17 |
| 39 days | 1821 ± 62 | | 1754 ± 58 |
| 44 days | 2150 ± 79 | | 2053 ± 69 |
| Metatarsus Length[2] | 87.3 ± 0.9 | | 81.9 ± 1.0 |
| | | $p < 0.005$ | |
| Liver Wt.[3] | 2.2 ± 0.0 | | 2.2 ± 0.1 |
| Abdominal Fat Wt.[3] | 3.0 ± 0.2 | | 2.5 ± 0.3 |
| Spleen Wt.[3] | 0.16 ± 0.0 | | 0.13 ± 0.0 |
| Bursa of Fabricius Wt.[4] 100 g | 75 ± 7 | | 65 ± 13 |
| Testes Wt.[5] | 587 ± 91 | | 529 ± 71 |
| Skin Strength[6] | 901 ± 59 | | 769 ± 47 |
| | | $p < 0.05$ | |
| Skin % Water | 28.0 ± 1.7 | | 29.5 ± 3.2 |
| Skin % Fat | 56.1 ± 2.5 | | 55.7 ± 2.7 |

Superscripts:
[1]weight in grams.
[2]length in millimeters.
[3]Expressed as grams per 100 grams (g/100 g).
[4]Expressed as milligrams per 100 grams (mg/100 g).
[5]weight in milligrams.
[6]skin breaking strength in grams.

Preparative Example 3

Purified, lyophilized ovine PRL was obtained from Sigma Chemcial Company (USA) and dissolved in alkaline physiological saline (0.9%). This was then adjusted th physiological pH. Fresh material was prepared every two days and stored at 4 degrees C. Concentration was adjusted for use in the Biological Examples 5 and 6 so as to provide the daily dose in 0.3 ml of medium.

Preparative Example 4

Purified, lyophilized human pituitary GH (Wellcome, UK) was dissolved in physiological saline (Wellcome, UK). Fresh material was prepared every two days and stored at 4 degrees C. Concentration was adjusted for use in Biological Examples 5 and 6 so as to provide the daily dose in 0.3 ml of medium.

Biological Example 5

Cross-bred male, day-old c ckens of a heavy breed were obtained from a com rcial source and after brooding under standard conditions to the age of fourteen days were housed in standard cages (two birds to a cage, one bird of which was from the Group treated with ovine Prolactin, one from the Control Group) in an environment controlled at levels of temperature and moisture conventional for age. The chicks were kept on continuous white fluorescent lighting, which varied from 80-120 lux according to cage position. Feed and water was provided ad libitum. Nutrient content of feed was commercially conventional. Birds in experimental and control groups were paired for weight. Initial mean metatarsal length of the two groups was dissimilar, so final length is reported as percent increase in length. After a period of four days for adaptation to cages, injection of prolactin i.m. in the leg was started at 18 days of age and continued for 12 days, the birds receiving 1.6u/100 gm of body weight at 7:00 a.m. Control birds were injected with physiological saline. Birds were weighed individually at 30 days when the experiment was terminated. The length of the metatarsus was measured and its weight also recorded after the birds were killed by cervical dislocation. Abdominal tissues were removed and weighed.

Treated birds gained 6.8% more weight than controls. Relative increase in metarsal length was more than 8% greater in the treated birds.

Statistical Evaluation

Arithmetic means and standard errors were calculated using conventional methods. Differences between groups were identified by Student's t-test.

TABLE 2

The Effect of Prolactin on Growth and Other Parameters in Male Broilers.

| | Prolactin | | Control |
|---|---|---|---|
| Initial Body Wt.[1] | 667 ± 9 | | 667 ± 9 |
| Final Body Wt.[1] | 1322 ± 20 | | 1237 ± 19 |
| | | ($p < 0.05$) | |
| Length % Increase[2] | 144.0 ± 3.1 | | 133.2 ± 2.7 |
| | | ($p < 0.05$) | |
| Metatarsal Wt.[3] | 33 ± 1 | | 31 ± 1 |
| Liver Wt.[4] | 2.8 ± 0.1 | | 2.7 ± 0.2 |
| Abdominal Fat Wt.[4] | 2.0 ± 0.5 | | 1.5 ± 0.4 |
| Testes Wt.[5] | 23 ± 38 | | 370 ± 67 |

Superscripts:
[1] weight in grams (g).
[2] length percent increase is in metatarsal length.
[3] weight is in grams.
[4] expressed as grams per 100 grams (g/100 g BW).
[5] weight in milligrams (mg).

Biological Example 6

Cross-bred, male, day-old chicks of a heavy breed (Anak) were obtained from a commercial source and after brooding under standard conditions to the age of three weeks, were allocated randomly to one of three groups: (1) ovine Prolacitn treatment (PRL); (2) human Growth Hormone treatment (GH); and (3) treatment with physiological saline (Control —C). One bird from each group was allocated to a cage (i.e., three birds per cage). The birds were maintained as described in Biological Example 1 above. At four weeks, the birds were found to range in weight from 825-1025 grams. From this time, injections were given i.m. (intramuscular) daily at 7:00 a.m. for seven days. The PRL group received 1.6 I.U. Prolactin per 100 grams of body weight, the GH group received 0.2 I.U. human pituitary Growth Hormone and the C group received saline solution. At the end of the treatment period, the birds ranged in weight from 1100-1380 grams. The birds were killed by cervical dislocation. After plucking of sampling areas on the back and breast, skin samples were taken as follows:

Two small parallel incisions were made in the skin prior to removal from the carcass. The incisions were made using two Swan Morten No. 3 scalpels tightly bound together so as to maintain an exact and consistent distance of 5mm between the incisions. A rectangular piece of skin around the incisions was then removed, the longer side (about 10 centimeters) being parallel to the incisions.

The width of the samples was about 2 centimenters. Samples from the left and right side were taken from both back and breast. The samples were placed in an apparatus specially built for the purpose of testing torsional strength of skin. Further cuts were made at right angles to the incisions so that resistance to stretching of the skin could only come from the 5mm width of skin lying between the incisions. Using the given apparatus, the skin samples from the back were torn by the following mean applied weights:

| Chicken Group | Weight |
|---|---|
| Ovine Prolactin | 569 ± 38 grams |
| Human Growth Hormone | 586 ± 43 grams |
| Controls (saline) | 447 ± 43 grams |

As analysed by Student's t-test, both treatments caused an increase in skin strength ($p < 0.05$) compared to that in the Control birds. PRL-treated skin was 27% stronger and GH-treated birds 31% stronger. Samples from the breast showed the same trend, though it was not statistically significant.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for stimulating skeletal growth in normal poultry as evidenced by increased metatarsal length of treated poultry comprising administering a growth stimulating amount of prolactin to said poultry.

2. A method according to claim 1 wherein said prolactin is ovine prolactin.

3. A method according to claim 1 wherein said prolactin is chicken prolactin.

4. A method according to claim 1 wherein doses of about 2 to about 3 i.u. of prolactin per 100 gm of body weight are administered for about 10 to 30 days.

5. A method according to claim 1 comprising administering both prolactin and growth hormone to said poultry.

6. A method according to claim 5 comprising first administering prolactin to young poultry for up to about 21 days and then subsequently administering growth hormone.

7. A method according to claim 5 comprising jointly administering prolactin and growth hormone to said poultry.

* * * * *